United States Patent [19]
Kwa et al.

[11] Patent Number: 5,171,979
[45] Date of Patent: Dec. 15, 1992

[54] DEVICE FOR SCANNING CONTAINERS FILLED WITH LIQUID

[75] Inventors: Paul T. H. Kwa, Fellbach; Juergen Wagner, Stuttgart, both of Fed. Rep. of Germany

[73] Assignee: Eastman Kodak Company, Rochester, N.Y.

[21] Appl. No.: 732,248

[22] Filed: Jul. 18, 1991

[30] Foreign Application Priority Data

Jul. 20, 1990 [DE] Fed. Rep. of Germany ....... 4023149

[51] Int. Cl.$^5$ .............................................. G01N 9/04
[52] U.S. Cl. ................................. 250/223 B; 356/240
[58] Field of Search ............ 250/223 R, 223 B, 214 R, 250/222.1; 209/523, 524, 529; 356/240; 53/53, 72

[56] References Cited

U.S. PATENT DOCUMENTS

| | | | |
|---|---|---|---|
| 3,477,197 | 11/1969 | Budz | 209/529 |
| 4,253,573 | 3/1981 | Dubberly et al. | 209/525 |
| 4,259,571 | 3/1981 | Dubberly | 209/524 |
| 4,807,162 | 2/1989 | Shibayama et al. | 356/240 |
| 4,885,461 | 12/1989 | Mattila et al. | 250/223 B |

FOREIGN PATENT DOCUMENTS

185330 6/1986 European Pat. Off. .
96065 9/1986 European Pat. Off. .
90/08307 7/1990 World Int. Prop. O. .

Primary Examiner—David C. Nelms
Assistant Examiner—K. Shami
Attorney, Agent, or Firm—Dana M. Schmidt

[57] ABSTRACT

An analyzer is described comprising a device for scanning containers filled with body fluid and held in a tray, the openings of which are sealed by means of a sealing member, e.g. a stopper or cup. The opto-electronic scanning device consists of a receiver and a transmitter comprising a plurality of vertically arranged receiver elements and transmitter elements, respectively, facing each other in a registered manner. Receiver and transmitter are arranged on a pivotable transport path for the containers between an input station and two processing stations. During the transport of container through the scanning device, the intensity of the scanning beam of the transmitter elements can be controlled from a low to a high level by means of a control unit comprising a microprocessor. Shape and/or size of the sealing member is thereby detected by means of the low intensity and transmittance or type of the sealing member by means of the high intensity. In this way, the transport direction of the containers can be controlled such that a container having a stopper is moved to an opening means and a container with or without a cup is moved to an aspirator for body fluids.

18 Claims, 11 Drawing Sheets

DEVICE FOR SCANNING CONTAINERS FILLED WITH LIQUID

FIELD OF THE INVENTION

The present invention relates to a device for scanning containers filled with liquid and arranged in a tray, in particular test tubes filled with body fluids the openings of which are sealed by means of a sealing member, said tubes being fed to various processing stations within an analyzer.

BACKGROUND OF THE INVENTION

Analyzers featuring automatic scanning means are known which can process a number of samples to be analyzed.

EP-PS 0 096 065 discloses a means for automatically scanning test tubes which are held in an elongated tray and fed to a processing station in which the presence or absence of a test tube in the tray is detected by means of an opto-electronic sensor means. For this purpose, the side walls of the individual test tube receptacles are provided with apertures.

SUMMARY OF THE INVENTION

It is therefore the object of the invention to provide a generic device by means of which the type, shape and size as well as the transmittance of a sealing member covering a container can be detected and by means of which—in response to such detection—the containers are fed to various processing stations. In general, the sample processing rate is to be considerably increased in order to meet the requirements for a quick and reliable diagnosis.

The above object is attained in that the scanning device is an opto-electronic device consisting of a transmitter and a receiver, and in that the transmitter and the receiver comprise a plurality of vertically arranged transmitter elements and receiver elements, respectively, facing each other in a registered manner. The scanning beams produced between the transmitter elements and the receiver elements are controlled in an advantageous manner by means of a control unit consisting of a microprocessor, input and output circuit arrangements, and a memory.

In this conjunction, the signals produced by the scanning means in response to the shape and size as well as the transmittance or type of a sealing member are fed to the microprocessor and used for controlling the processing stations.

Using the device according to the invention, the problem is solved in an advantageous manner in that the shape and size of a stopper as well as the type of a cup also containing body fluid can be detected. The signals obtained are further processed so as to feed the containers having different sealing members to their predetermined processing stations. This means that reliable, flexible and quick processing of the supplied samples of patients' body fluids is warranted and thus a clear medical diagnosis can be given after a short time.

The device according to the invention will now be described in detail with reference to an embodiment shown in the drawing and the sub-claims.

DESCRIPTION OF THE PREFERRED EMBODIMENTS

Figure 1:
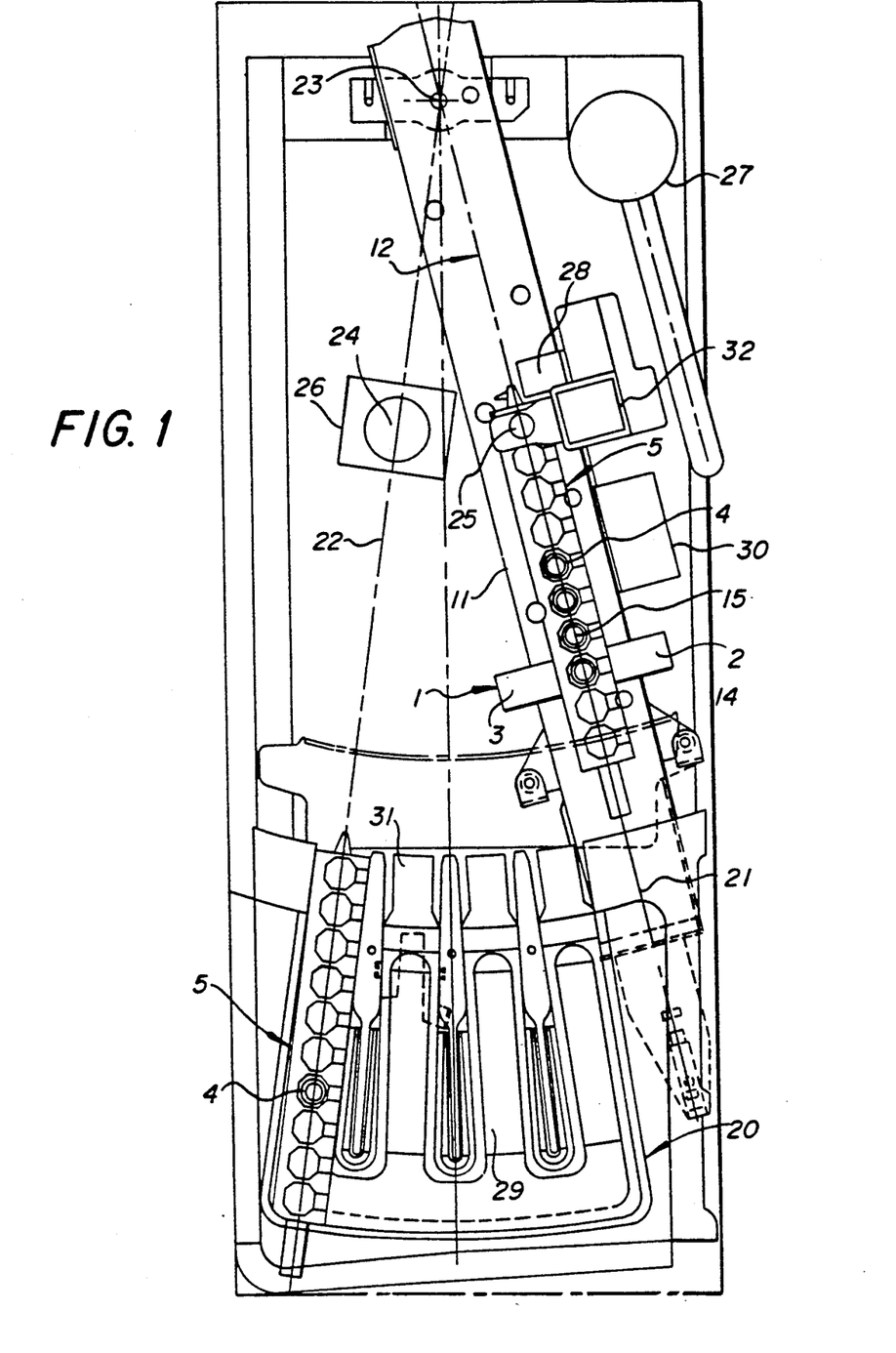
FIG. 1 shows a top view of the device according to the invention in an analyzer comprising an input station, a transport path and two processing stations.

An analyzer shown in FIG. 1 consists of an input station 20 comprising four tray tracks 29 arranged side by side for inserting elongated trays 5 carrying test tube containers 4, a transport path 12 formed as an elongated housing 11 which is pivotable about a fulcrum 23 and can be aligned with each of the tray tracks 29 and with a zero position 21, and two processing stations 24 and 25 arranged about halfway down the transport path 12 which is approximately twice as long as a tray 5.

A scanning device 1 for scanning a sealing member 8 inserted in container 4, a patient's data scanner 30 reading the data provided on container 4, and a laterally guided, longitudinally movable tray movement hook 28 for moving the tray 5 from the input station 20 to one of the two processing stations 24 and 25 and back, are arranged along the transport path 12 and connected to housing 11.

The scanning device 1 is arranged at the end of the transport path 12 facing the exits 31 of the tray tracks 29 and mounted in a position in which all containers 4 of tray 5 can be scanned before the first container, during the transport from the input station 20 to one of the two processing stations 24 and 25, has reached said stations. The information ascertained by device 1 as processed by microprocessor 43 is relayed to and used by container opening means 26.

The scanning device 1 consists of a transmitter 3 and a receiver 2 which are laterally arranged at the transport path and associated with one another such that scanning beams 14 can be generated between them in the form of light barriers.

In the processing station 25 associated with the zero position 21 of transport path 12 an aspirator 27 is arranged with a proboscis 33 for removing body fluid from container 4, and a centering/detecting means 32 for the tray 5.

The second processing station 24 is arranged in a final position 22 (facing the zero position 21) of transport path 12 featuring an opening/closing means 26 for the containers 4.

Figure 2:
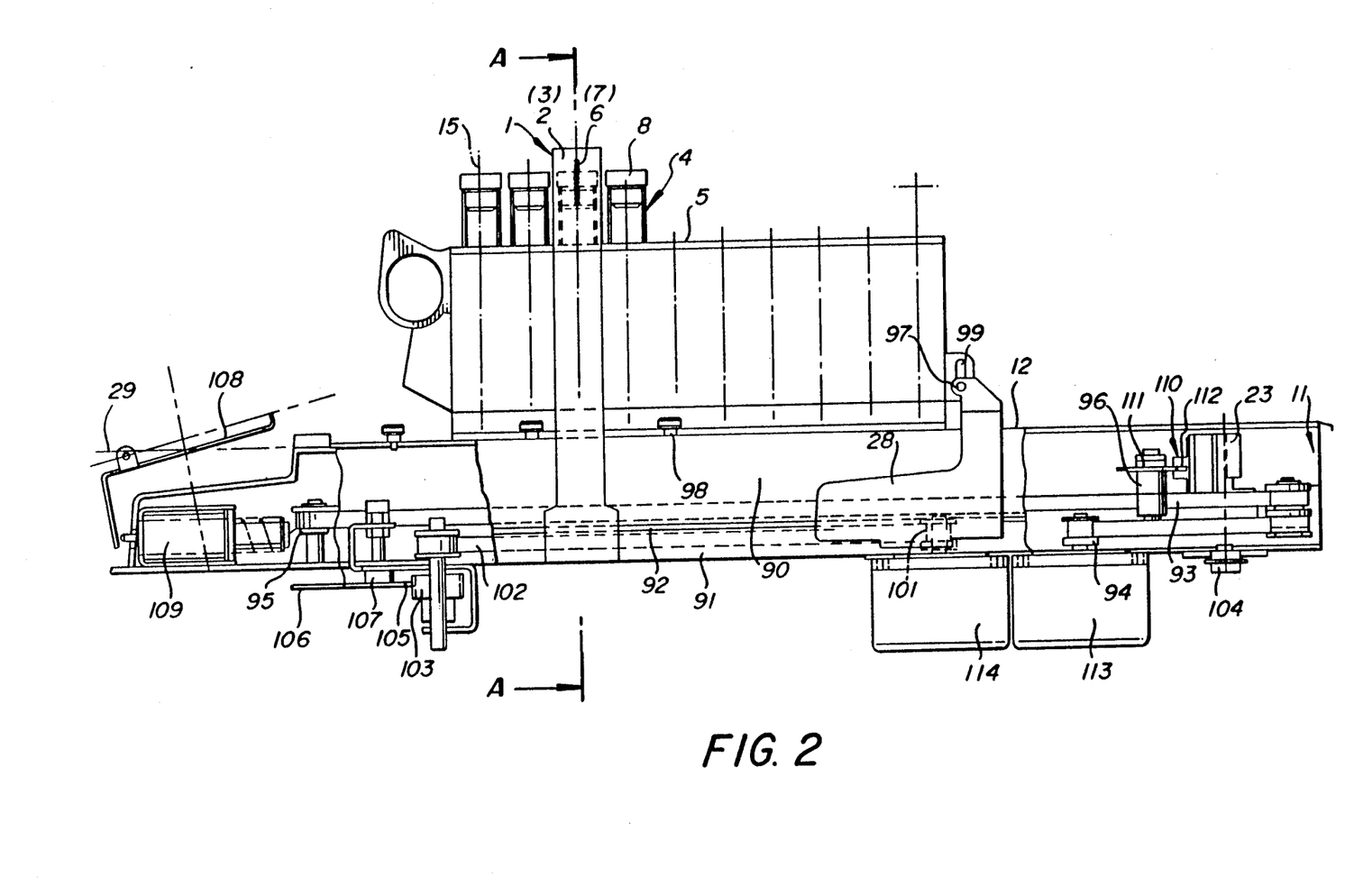
FIG. 2 is a partial view of the scanning device according to FIG. 1 showing a tray equipped with containers.

FIG. 2 shows a scanning device 1 comprising a tray 5 positioned on transport path 12 and equipped with containers 4 as well as the tray movement hook 28 with its drive elements and a pulse generator 110. Tray 5 is in a position in which the vertically extending central axis 15 of one of the containers 4 intersects the optical axis 16 between receiver 2 and transmitter 3. In this case, the container is provided with a sealing member 8.

Receiver 2 and transmitter 3 of scanning device 1 consist of a plurality of vertically aligned receiver elements 6 and transmitter elements 7, respectively, which are horizontally associated with each other and are arranged above the upper edge of tray 5 in the area of the sealing member 8 of container 4. In front of each receiver element 6 and transmitter element 7 an aperture 13, 13' is arranged which is centered to the optical axis 19. Both the receiver and the transmitter are constructed so that the topmost element projects above the tallest container that is expected. Stated in other words, if the uppermost receiver element 6 is blocked by container from receiving the light beam from its corresponding uppermost transmitting element 7, an error message is generated.

FIG. 2 shows drive elements for pivoting the transport path, the arrangement and operation of said elements being described below.

Housing 11 of transport path 12 is substantially closed on all sides and consists of a housing portion 90 of a U-shaped cross-section and a bottom portion 91 of L-shaped cross-section which are connected such that a longitudinal opening 92 is created.

The lower portion of the tray movement hook 28 extends through said opening 92 into the interior of housing 11 and is connected with a toothed belt 93 which is arranged in this area.

Beneath bottom portion 91 a stepping motor 113 is mounted which by means of a drive wheel 94 and a deflecting roller 95 drives the toothed belt 93 and thus the tray movement hook 28.

An encoder wheel 111 the rotary movement of which is detected by a sensor 112 designed as a light barrier is mounted to the drive shaft 96 driven by the stepping motor 113 by means of the toothed belt. Encoder wheel 111 and sensor 112 represent the pulse generator 110.

A hook 97 is mounted to the upper portion of tray movement hook 28 which hook 97 extends horizontally beyond the centerline of transport path 12 above the guide pins 98 and, for advancing tray 5, engages with an eyelet 99 arranged at the tray's end face.

An additional stepping motor 114 arranged next to the stepping motor 113 and also mounted to the bottom portion 91 drives a pinion 103 for pivoting transport path 12 about a pin 104 or fulcrum 23 by means of a drive gear 101 and a toothed belt 102. Pinion 103 thereby engages a arc-shaped rack 105 which in the area of the exits 31 of the tray track 29 is connected to support plate 106.

Two bearing supports 107 and 107' are arranged on said support plate 106 which are mounted to the housing 11 of transport path 12 and during the pivotal movement of the transport path 12 slide thereon.

A retaining means 108 associated with each of the exits 31 of the tray track 29 can be activated by an electromagnet 109.

Figure 3:
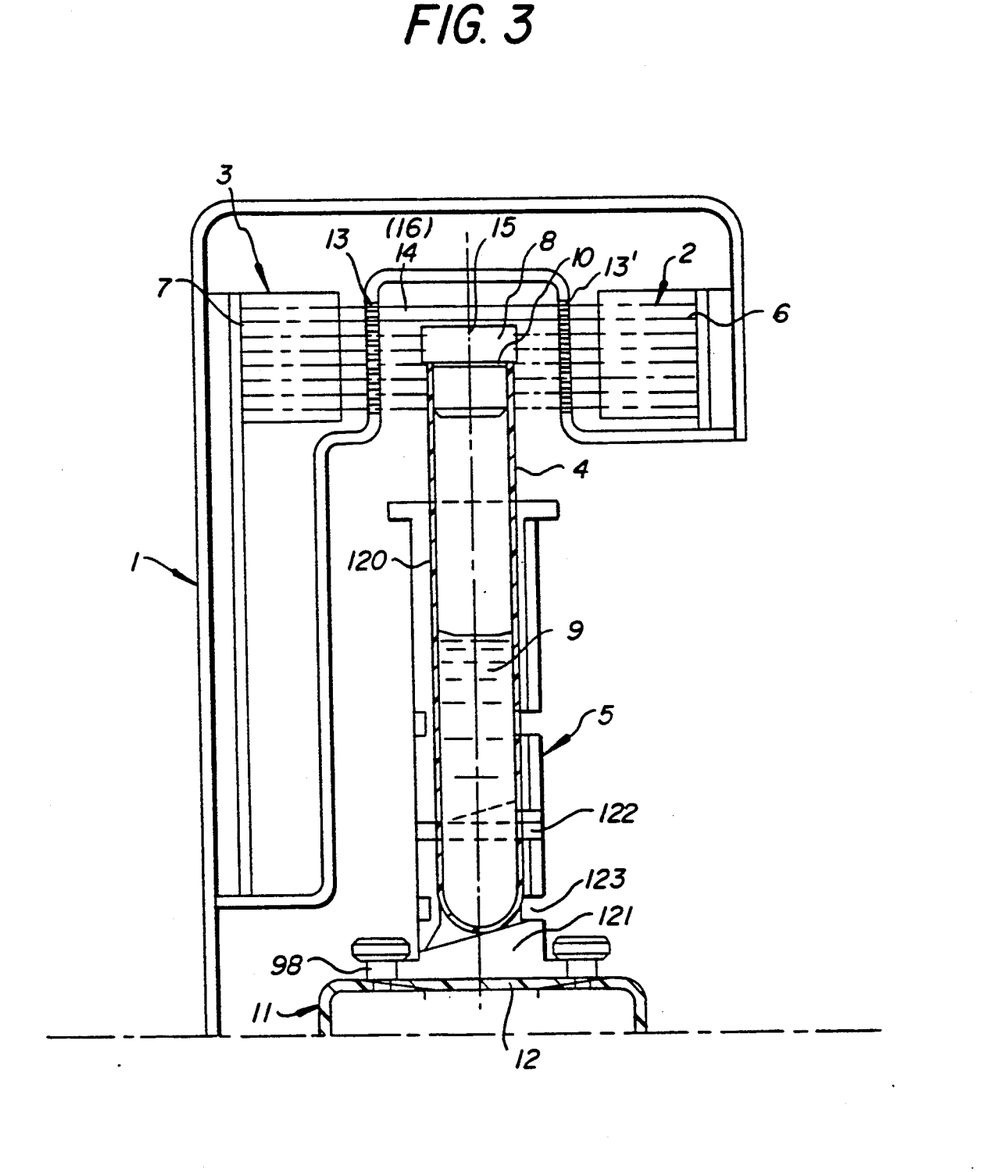
FIG. 3 is a cross-section along the line A—A in FIG. 2 of the scanning device according to FIG. 1 comprising a transmitter and a receiver.

FIG. 3 shows the scanning device 1 and a tray 5 with one of the containers 4 having a sealing member 8.

The transmitter elements 7 are shown in an activated condition in which they transmit a scanning beam 14 along the optical axis 19 through the apertures 13 and 13' to reach the receiver elements 6.

In the area of the sealing member 8 and the container 4, the scanning beam 14 is absorbed and/or reflected so that it does not reach the receiver element 6.

The apertures 13 and 13' have a diameter and a distance to the transmitter/receiver elements which are dimensioned such that, on the one hand, the scanning beam 14 of the transmitter element 7 can be confined and, on the other, only a scanning beam 14 associated with the respective receiver element 6 and coinciding with the optical axis can be received by the receiver element 6.

Furthermore, each of the emitters of transmitter element 7, and each of the detectors of receiver 6 are spaced apart vertically a distance that is equal to or smaller than the smallest distance in heights that are available in differing sealing members. The purpose is to distinguish, thereby, as to which kind of sealing member 8 is present. That is, a rubber sealing member has a height, created by its upper shoulder, that is different from the height of the plastic sealing members. By spacing the emitters and detectors by a height $\leqq$ to this difference in heights, the scanner is able to tell which kind of stopper is present, and relay that information to opening means 26.

By means of tray 5, the container 4 provided with a sealing member 8 is kept at a level in which at least one scanning beam 14 extends above sealing member 8. The container opening 10 is always arranged at the same height. For this purpose, the tray 5 features several horizontally arranged slots 123 along one longitudinal side thereof which are provided at different heights.

For containers 4 which are smaller than the maximally admissible height, an adapter platform 122 is—depending on the height of the containers—inserted in an appropriate slot 123 for height adjustment. The containers 4 then rest on the adapter platform 122 extending into the receptacles 120 of tray 5.

Figure 4A:
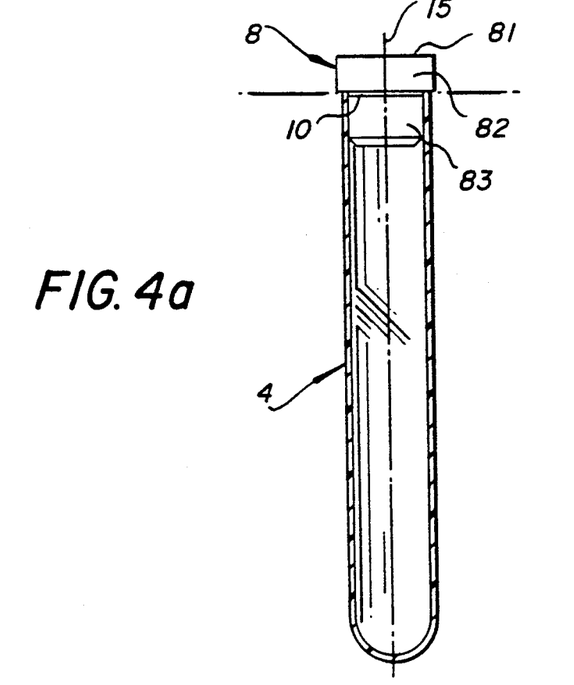
FIG. 4a is a partial view of a container according to FIG. 2 including a stopper.
Figure 4B:
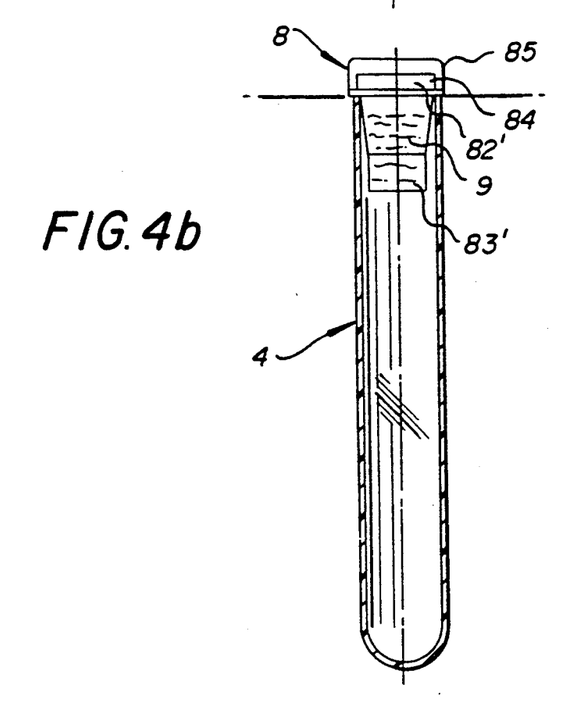
FIG. 4b is a partial view of a container according to FIG. 2 including a cup.

FIGS. 4a and 4b show two different sealing members 8 each sealing a transparent container 4.

The first type of sealing member 8 is represented by a stopper 81 consisting of an opaque deformable rubber or plastic material. The stopper 81 comprises a cylindrical upper portion 82 and a cylindrical lower portion 83, said upper portion 82 having a diameter which is equal to or larger than the outer diameter of container 4, and said lower portion 83 having a diameter which is about equal to the inner diameter of container 4.

The second type of sealing member 8 is represented by a cup 84 consisting of transparent plastic material and also comprising an upper portion 82' and a lower portion 83'. Both portions are however designed as hollow cylinders with the lower portion 83' being sealed at its lower end and having a diameter which is smaller than the inner diameter of container 4.

In general the upper portion 82' of cup 84, with respect to that of stopper 81, is smaller in height. The lower portion 83' of cup 84 is however larger in height than that of stopper 81 and substantially smaller than the height of container 4. Cup 84 is used for receiving a minor amount of body fluid 9.

The device operates as follows:

First, one or several trays 5 equipped with containers 4 or test tubes are inserted into the four tray tracks 29 of the input station 20. The individual containers 4 are either filled with body fluid 9 themselves and sealed by a stopper 81 or carry a cup 84 filled with body fluid 9 and sealed by a lid 85. Each container 4 is associated with patient's data in the form of a bar code on a sticker and with special processing instructions for analyzing the body fluids. Such data are collected at the beginning of a patient's medical examination and entered in an operating memory 44 of an electronic control unit 40 shown in FIG. 5 when the containers 4 are inserted in the input station 20.

Figure 5:
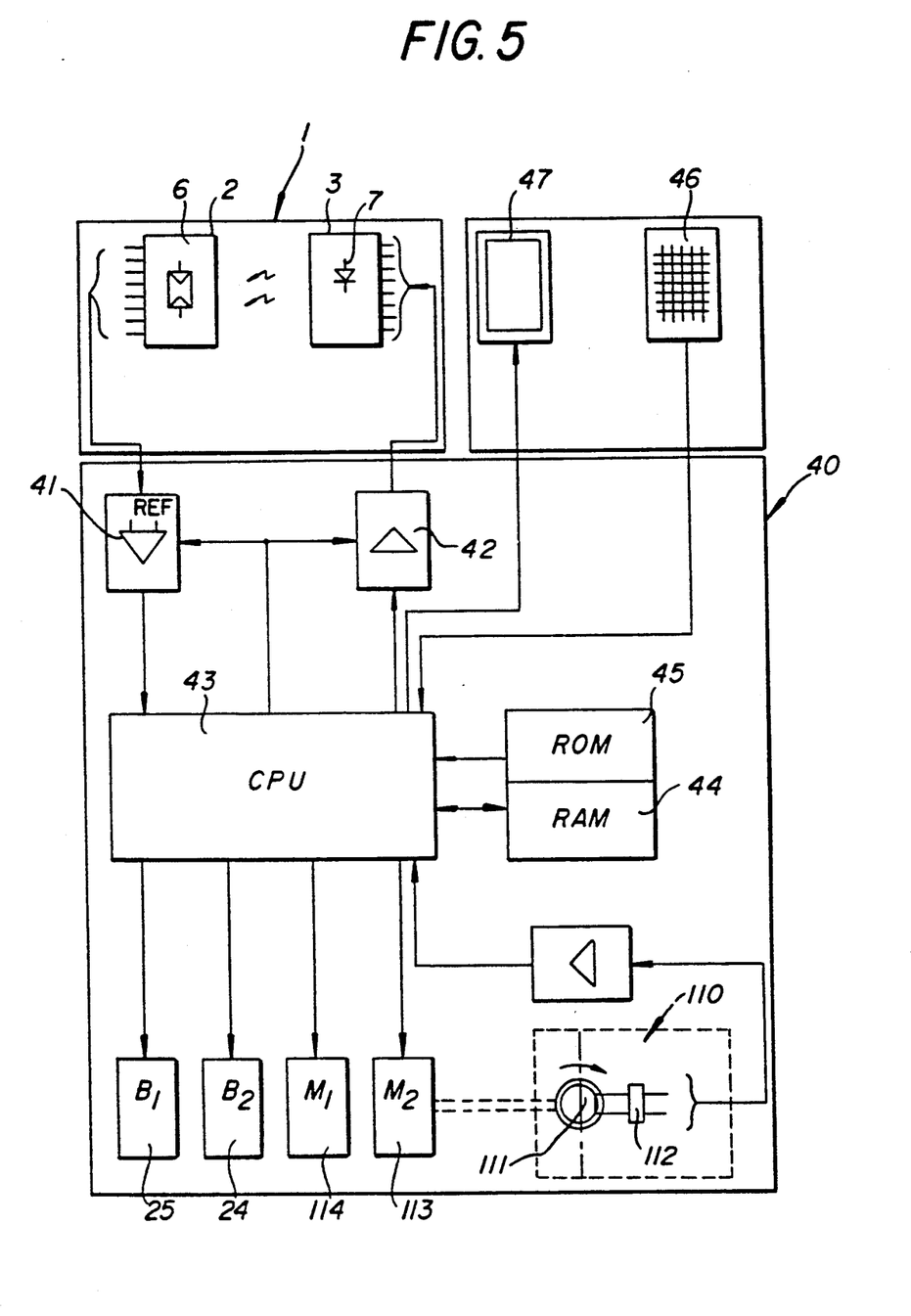
FIG. 5 shows a block diagram of a control unit.

If now by means of a keypad 46 of control unit 40 a processing procedure is started, said procedure automatically runs in accordance with a program stored in a program memory 45 and with the processing instructions of the operating memory 44 in cooperation with a microprocessor 43.

After starting the processing procedure, the transport path 12 driven by the stepping motor 114 is pivoted to the tray track 29 of input station 20 holding tray 5 with the containers 4 which according to the program are next to be processed.

During this procedure, the tray movement hook 28 driven by the stepping motor 113 is moved towards the input station 20 so that hook 97 can engage with the eyelet 99 of tray 5 when transport path 12 has reached the selected tray track 29. When the transport path 12 is aligned with the tray track 29, the retaining means 108 is pivoted downwards out of its exit 31 and tray 5 including the containers is moved onto the transport path 12 by means of the tray movement hook 28. During this transport movement tray 5 passes through the scanning device 1, so that all containers 4 carrying sealing members 8 are scanned until tray 5 has completely been moved onto the transport path 12.

The scanner 30 arranged downstream of the scanning device 1 thereby detects the patient's data. All data detected by the scanning device 1 and the scanner 30 are stored in the operating memory 44 and used in cooperation with the microprocessor 43 for controlling the various functions of the analyzer.

In response to the data detected by the scanning device 1, the transport direction of the containers 4 carried in tray 5 or the transport path 12 is controlled, as well as the functions of the processing stations 24 and 25.

Scanning of the sealing member 8 of a container 4 is performed as follows:

When the container 4 together with the sealing member 8 reaches the scanning beams 14 of the transmitter elements 7, they are interrupted on their way to the receiving elements 6 by the sealing member 8 and container 4 according to their vertical lateral profile.

The signals produced by the receiving elements 6 thus provide an adequate profile of the sealing member 8 and the container 4 in the form of their signal amplitudes. In this connection, a low signal amplitude 52 represents an interrupted, i.e. absorbed, or reflected scanning beam 14, whereas a high signal amplitude 53 represents an uninterrupted scanning beam (see FIGS. 6a and 6b). At this time, i.e. in this position of the container 4, all transmitter elements 7 transmit at a low intensity 50 (see FIG. 6c).

Figure 7A:
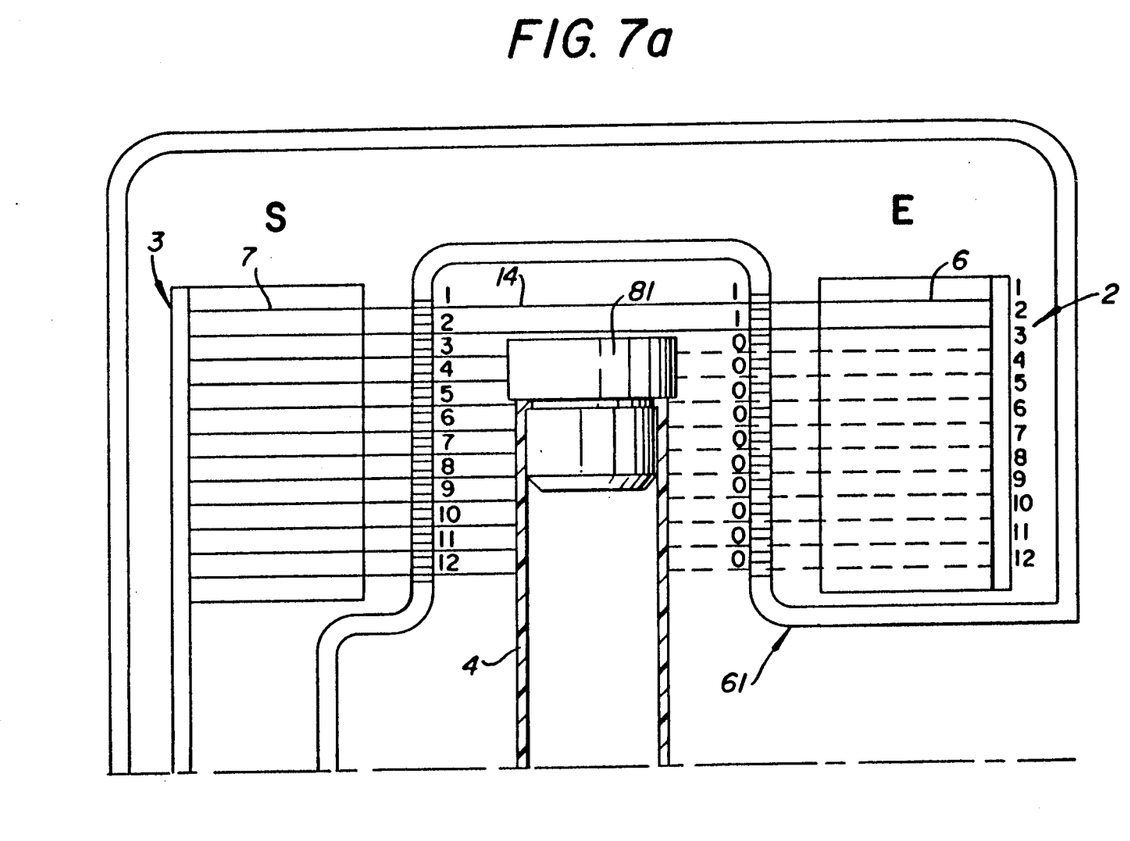
FIGS. 7a and 7b show a signal pattern of all receiver elements in response to the type of the sealing member when a low intensity scanning beam is applied.
Figure 7B:
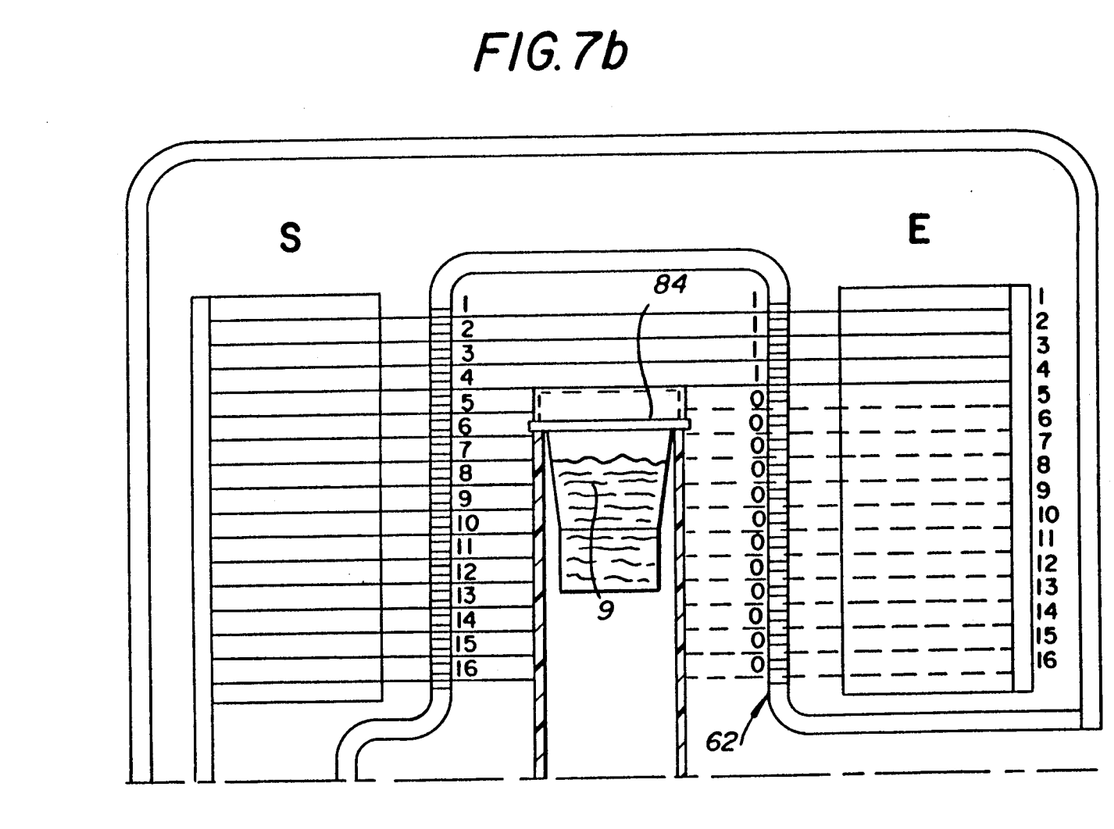

By means of an input circuit 41 of control unit 40 the signals of the receiving elements 6 are brought to a predetermined level adequate for operating the microprocessor 43 and stored as a signal pattern 61 or 62 in the operating memory 44 representative of a container 4 or its position in tray 5 (see FIGS. 7a and 7b). Circuit 41 is a conventional comparator circuit such as a Schmitt trigger, with an adjustable threshold. Preferably, circuit 41 includes means for limiting the input signal generated under the high beam intensity, such as by using a Zener diode.

Figure 6A:
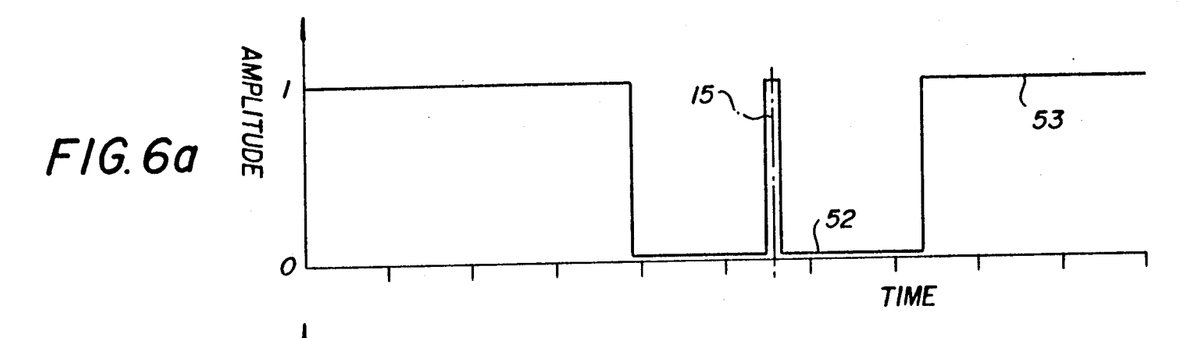
FIGS. 6a to 6c represent diagrams showing the signal response of a receiver element as a function of the intensity of a scanning beam, the transport path and the type of the sealing member.
Figure 6B:
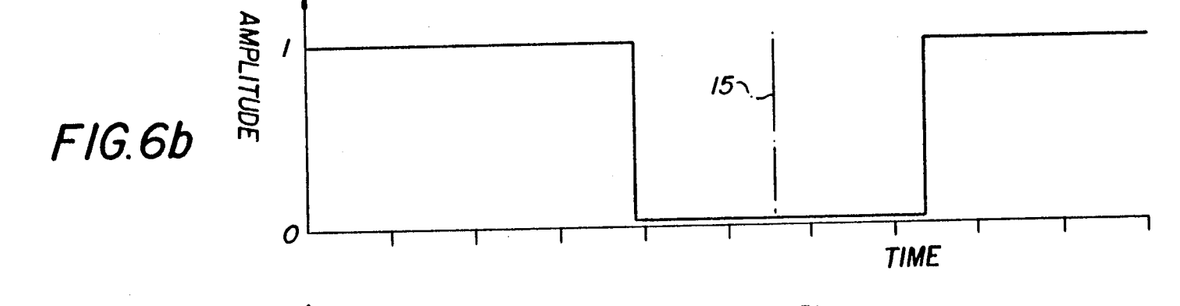
Figure 6C:
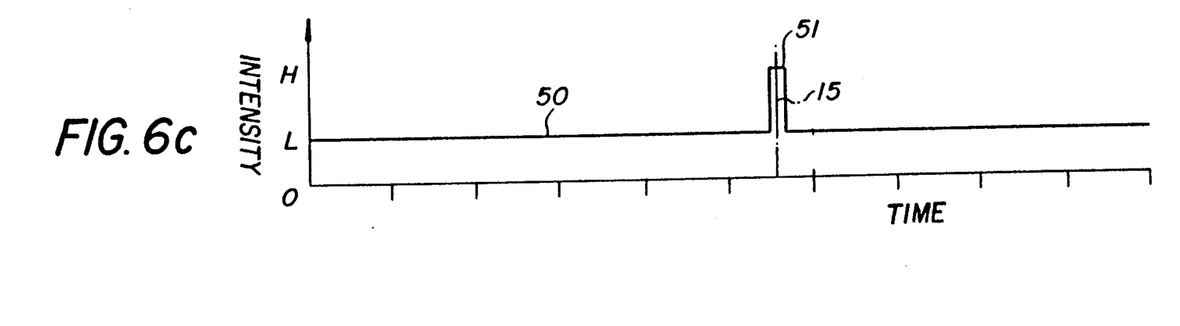

When during its continuous transport through the scanning device 1 the sealing member 8, i.e. the container 4, reaches with its vertical central axis 15 the scanning beam 14 of transmitter elements 7, the control unit 40, by means of an output circuit 42, controls the scanning beam 14 to produce a high intensity 51 (see FIG. 6c).

The high intensity is adjusted such that a cup 84 filled with body fluid 9 is transilluminated by the scanning beam 14 through the container 4, whereas a stopper 81 is not transilluminated (see FIGS. 6a and 6b). The radiation effective to perform the function is infrared radiation.

Most preferably, the high intensity is at a value that is from 5 to 10 times the value of the low intensity.

Figure 8A:
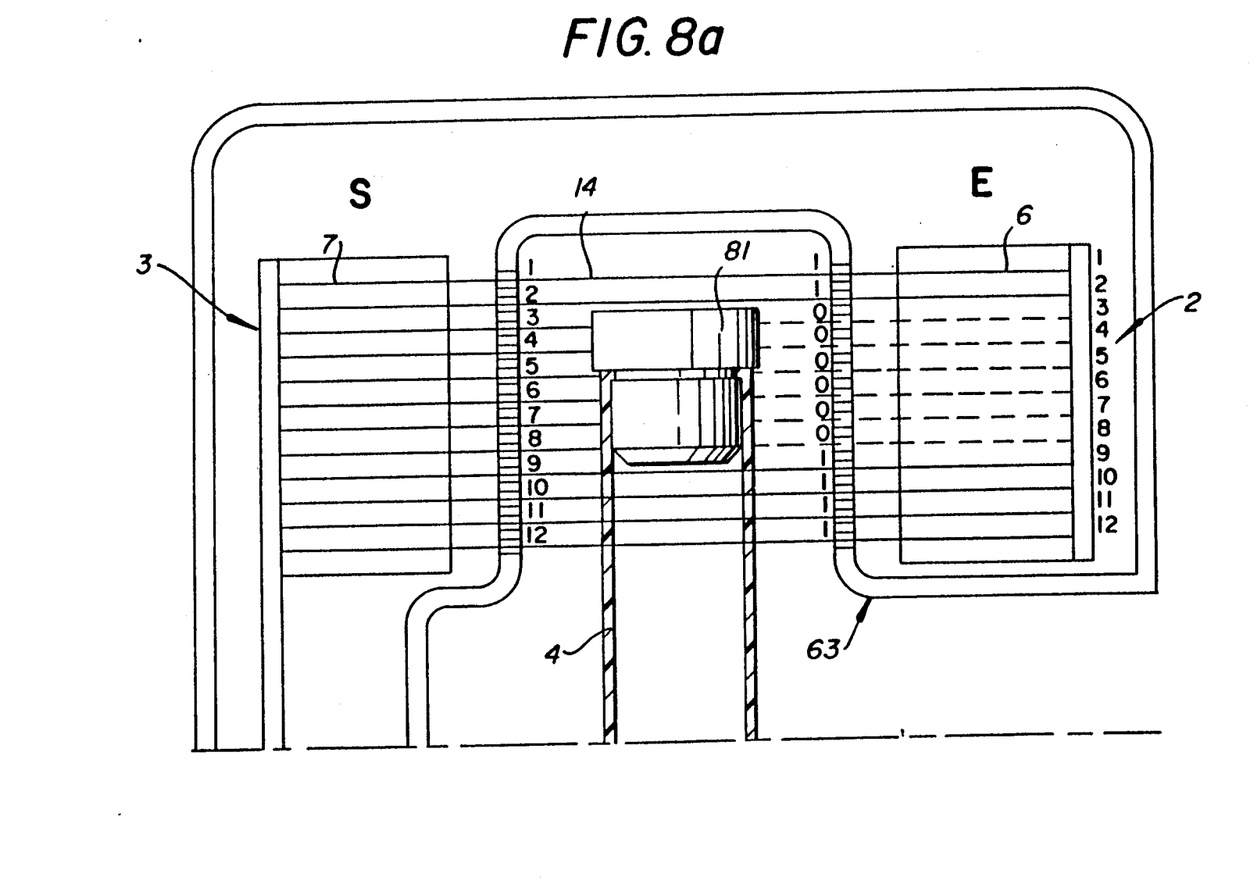
FIGS. 8a and 8b show a signal pattern of all receiver elements in response to the type of the sealing member when a high intensity scanning beam is applied.
Figure 8B:
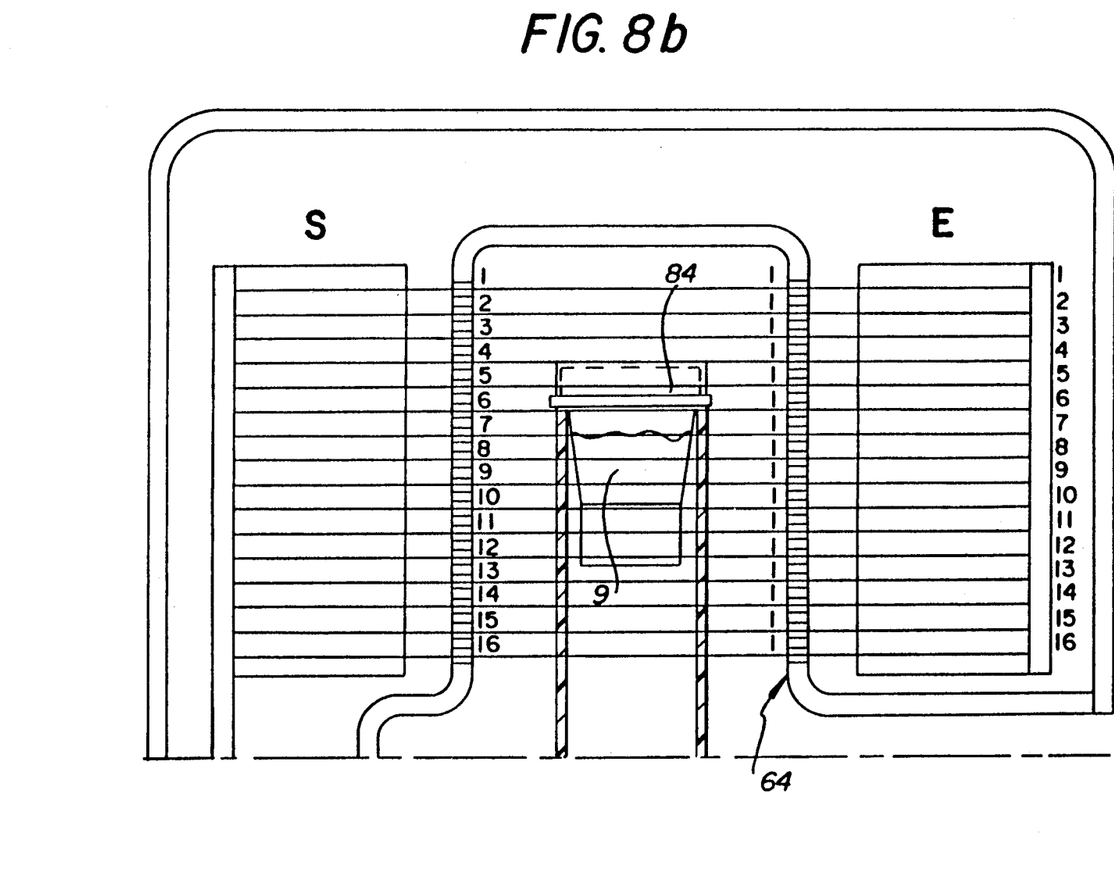

As a result of the high beam transmission, an additional signal pattern 63 and 64, respectively, is generated in the receiver 6 (see FIGS. 8a and 8b).

As soon as said additional signal pattern 63 and 64, respectively, delivered by the receiver elements 6 is detected and stored, the scanning beam 14 is controlled to show a low intensity 50 (see FIG. 6c).

Association of the signal patterns obtained with containers 4 and association of the intensity change-over related to a container diameter are effected via the distance travelled by tray 5 and by the tray movement hook 28, respectively. For this purpose, pulses are produced by the pulse generator 110 connected to the drive system in response to said distance travelled said pulses being counted by the control unit 40 and, on the one hand, stored as address values associated with the signal patterns in the operating memory 44 and, on the other hand, fed to the microprocessor 43 as parameters for the intensity control.

The two signal patterns detected representative of a sealing member 8 are values which, by means of the microprocessor 43, are compared with the predetermined values contained in the program memory 45. Both the size and shape of containers with and without a sealing member are scanned and compared with such predetermined signal values stored in ROM 45. In FIGS. 7A & B, 8A & B, the height profiles are shown, 61–64, for, respectively, a stopper, a cup (low intensity only), and a stopper and a cup (high intensity).

If the values coincide, a further parameter is generated by the control unit 40 for controlling the pivoting direction of transport path 12 and for controlling the respective processing station 24 or 25, said parameter also being stored in the operating memory 44 and associated with the position of container 4 in tray 5.

By means of the comparison of the values, the presence of a container 4 with or without a sealing member 8 as well as the type of the sealing member 8 can be detected.

If the first scanned sealing member 8 is detected as being a stopper 81 and if tray 5 has completely been moved onto transport path 12, the pivoting of the transport path from the tray track 29 to the final position 22 is effected as well as the movement of the first container to processing station 24 including the opening means 26 for removing stopper 81.

Subsequently, transport path 12 pivots back to zero position 21 and, after centering container 4 and detecting its diameter, body fluid 9 is withdrawn in processing station 25 by means of aspirator 27, with the proboscis 33 moving to a lower liquid removal position.

The device operates differently when the sealing member 8 is detected as being a cup 84. In that case, the transport path 12 is directly pivoted to processing station 25 for removal of body fluid 9, with the proboscis 33 moving to an upper liquid removal position.

If the absence of a sealing member 8 is detected, the device operates as if a cup 84 were present, the proboscis 33 however moving to said lower liquid removal position.

If an inadmissible container 4 or sealing member 8 is detected, the operation is stopped and an error message appears on a display 47 (see FIG. 5).

Scanning, transport and processing of the other containers 4 held in tray 5 are also performed in the described manner.

Figure 9:
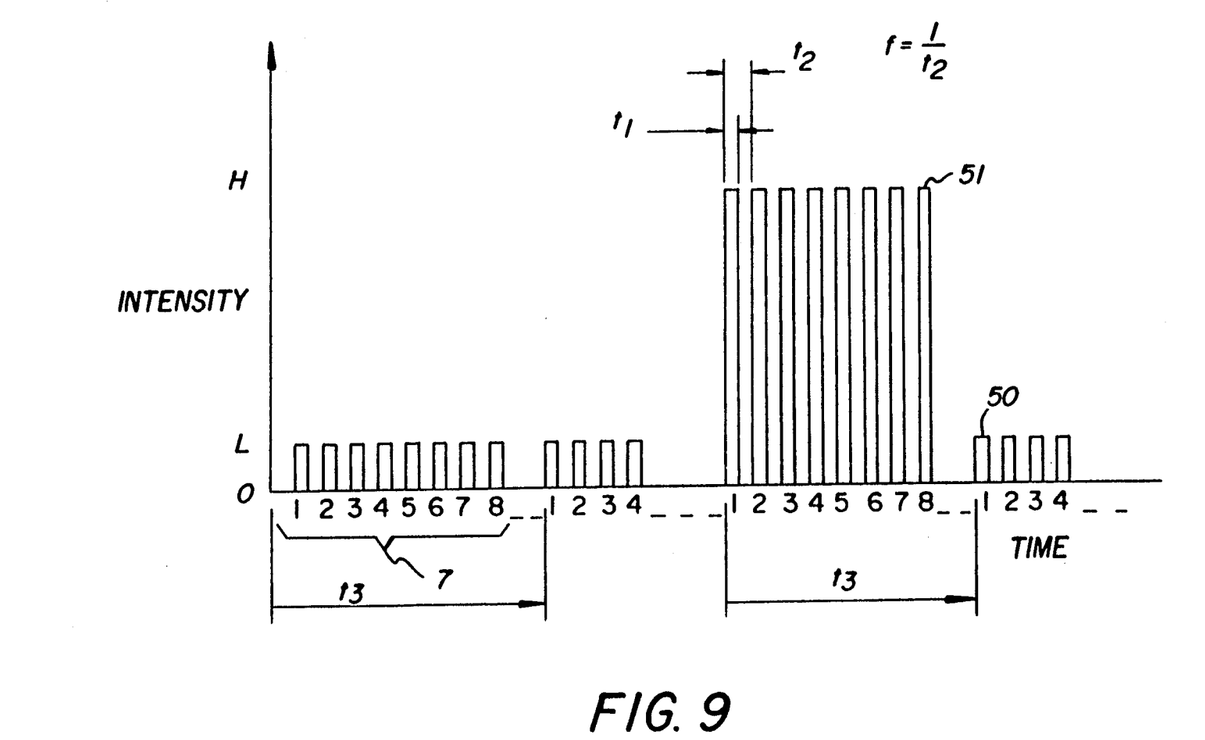
FIG. 9 is a diagram showing a clock-pulsed scanning beam between transmitter and receiver.

In a further advantageous manner, control unit 40 effects the sequential activation and deactivation of cooperating transmitter elements 7 and the receiver elements 6 continuously from top to bottom at a frequency that enables scanning the sealing member 8 and detecting the signal pattern 61, 62, 63, 64 during the continuous movement of container 4 on the transport path 12 (see FIG. 9).

In this way, interference effects such as ambient light, offset drift of the transmitter/receiver elements and their output/input circuits and undesired warm-up of the transmitter elements can be reduced.

The invention disclosed herein may be practiced in the absence of any element which is not specifically disclosed herein.

The invention has been described in detail with particular reference to certain preferred embodiments thereof, but it will be understood that variations and modifications can be effected within the spirit and scope of the invention.

What is claimed is:

1. In an electro-optical device in an analyzer for scanning moving containers that include open and closed containers randomly positioned in a support means each with liquid therein to be analyzed, said closed containers being sealed by a sealing member, said device comprising a transmitter and a receiver positioned to intercept at least the top of said moving containers;

the improvement wherein said transmitter and said receiver each comprise a plurality of vertically arranged elements, the elements of the receiver facing corresponding elements of said transmitter in a registered manner, the elements of both said transmitter and said receiver extending above the predetermined top of said containers, and wherein said transmitter is constructed to emit beams of at least two different intensities.

2. In an electro-optical device in an analyzer for scanning moving containers that include open and closed containers randomly positioned in a support means each with liquid therein to be analyzed, said closed containers being sealed by a sealing member, said device comprising a transmitter and a receiver positioned to intercept at least the top of said moving containers;

the improvement wherein said transmitter and said receiver each comprise a plurality of vertically arranged elements, the elements of the receiver facing corresponding elements of said transmitter in a registered manner, the elements of both said transmitter and said receiver extending above the predetermined top of said containers, and further including means for sequentially operating the elements of said transmitter.

3. A device according to claim 1 or 2, and further including means for discriminating between sealing members of different types.

4. A device according to claim 3, wherein said discriminating means comprise the spacing apart of the elements of said transmitter and said receiver a distance that is less than or equal to the smallest difference in height created by said different type sealing members.

5. A device according to claim 1 or 2, and further including control means for receiving electrical signals from said receiver and converting them to data representing the shape and size of any object at the end of a container that passes through the beam from said transmitter.

6. A device according to claim 5, wherein said control means comprise a microprocessor, input and output circuits, and operating and memory programs of said microprocessor.

7. A device according to claim 1, wherein said receiver generates a signal representative of the presence of absence of a sealing member, and said transmitter varies the intensity of said scanning beam in response to said signal.

8. A device according to claim 7, wherein said transmitter is constructed to transmit first at a low intensity beam to generate said signal from said receiver, and in response to the generation of a predetermined signal pattern by said receiver that is indicative of the presence of a sealing member, said transmitter is constructed to switch to a high intensity beam to detect the type of sealing member.

9. A device according to claim 8, wherein said high intensity has a value that is between 5 and 10 times the value of said low intensity.

10. A device according to claim 8, wherein said predetermined indicative signal is a digitized representation of the height profile of a container with or without a sealing member.

11. A device according to claim 8, and further including means for feeding individual ones of said containers to a first or a second processing station, depending on the pattern of said signal generated in response to said low intensity beam and said high intensity beam.

12. A device according to claim 1, and further including stop apertures for confining and limiting the size of an energy beam transmitted to said receiver.

13. A device according to claim 2 wherein said support means is a tray, and further including means for transporting a tray of containers along a transport path that moves transversely across the beams passing from said transmitter to said receiver.

14. A device according to claim 13, wherein said transporting means is pivoted about a fulcrum to allow said transport path to move from a zero position to a final position.

15. A device according to claim 14, and further including an aspirator disposed adjacent to said zero position, and a processing station comprising opening means for removing a sealing member from a container, disposed adjacent to said final position.

16. In a method for scanning a plurality of containers that are randomly positioned in a support means so as to be sealed or not sealed by a sealing member, to determine which are sealed, said method including emitting from a transmitter a scanning beam and receiving a beam whose intensity is different depending on whether a sealing member is present or not, the improvement wherein said emitting step includes the step of emitting sequentially a plurality of vertically spaced beams to a receiver having plural, vertically spaced detecting elements, and detecting the profile, as well as the existence, of any sealing member present.

17. A method according to claim 16 wherein said emitting step comprises first emitting a low intensity beam until a center line of a container is detected as being present, and then emitting a beam of intensity that is higher than said low intensity beam to detect the type of sealing member.

18. A method according to claim 17, and further including the steps of feeding individual ones of said containers to a first or a second processing station, depending on the pattern of signal generated in response to said low intensity beam and said higher intensity beam.

* * * * *

UNITED STATES PATENT AND TRADEMARK OFFICE
CERTIFICATE OF CORRECTION

PATENT NO. : 5,171,979
DATED : December 15, 1992
INVENTOR(S) : Paul T.H. Kwa, et al It is certified that error appears in the above-identified patent and that said Letters Patent is hereby corrected as shown below:

Column 8, line 28, change "of" (1st occurrence) to --or--

Signed and Sealed this

First Day of February, 1994

Attest:

BRUCE LEHMAN

Attesting Officer          Commissioner of Patents and Trademarks